United States Patent
Cooper et al.

(10) Patent No.: US 7,387,684 B2
(45) Date of Patent: *Jun. 17, 2008

(54) SINGLE-DOSE SPRAY SYSTEM FOR APPLICATION OF LIQUIDS ONTO THE HUMAN BODY

(75) Inventors: Steven C. Cooper, Athens, GA (US); Troy H. Cooper, Addison, TX (US); Ricky C. Croft, Dallas, TX (US)

(73) Assignee: Mystic Tan, Inc., Farmers Branch, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/841,396

(22) Filed: May 7, 2004

(65) Prior Publication Data

US 2005/0008577 A1 Jan. 13, 2005

Related U.S. Application Data

(60) Provisional application No. 60/469,289, filed on May 9, 2003.

(51) Int. Cl.
*B05C 11/10* (2006.01)

(52) U.S. Cl. .................. 118/684; 118/695; 118/696; 118/685; 118/681

(58) Field of Classification Search ............. 118/695, 118/696, 679, 680, 681, 684, 685, 300, 323; 604/289, 290, 296
See application file for complete search history.

(56) References Cited

U.S. PATENT DOCUMENTS

| | | |
|---|---|---|
| 1,982,509 A | 11/1934 | Frank |
| 2,954,146 A * | 9/1960 | Hullman ............ 222/630 |
| 4,004,733 A | 1/1977 | Law |
| 4,289,276 A | 9/1981 | Bollina et al. |

(Continued)

FOREIGN PATENT DOCUMENTS

EP 0 031 649 A2 7/1981

(Continued)

OTHER PUBLICATIONS

Cooper, S. C. and Law, S. E., "Electrostatic Sprays for Sunless Tanning of the Human Body", Proceedings of the ESA-IEEE Joint Meeting on Electrostatics, Jun. 25, 2003, pp. 1-12, University of Arkansas, Little Rock, Arkansas.

*Primary Examiner*—George Koch
(74) *Attorney, Agent, or Firm*—Gardere Wynne Sewell LLP (57) ABSTRACT

A spray device for coating a surface of a human body with a spray liquid, the spray device including at least one nozzle and at least one liquid container, wherein the at least one liquid container is adapted to hold a volume of spray liquid substantially equal to an amount required to apply a single dosage of the spray liquid for coating a surface of a human body. The spray device further includes a liquid channel adapted to connect the at least one liquid container to the at least one nozzle, and a spray valve adapted to cause the spray liquid to flow from the at least one liquid container to the at least one nozzle using the liquid channel. The spray device still further includes a control device adapted to control the operation of the spray device; and a mounting device for mounting the spray device to a mounting surface.

49 Claims, 7 Drawing Sheets

U.S. PATENT DOCUMENTS

| | | |
|---|---|---|
| 4,343,433 A | 8/1982 | Sickles |
| 4,357,900 A | 11/1982 | Buschor |
| 4,664,315 A | 5/1987 | Parmentar et al. |
| 4,688,518 A | 8/1987 | Missier |
| 4,731,058 A | 3/1988 | Doan |
| 4,846,525 A | 7/1989 | Manning |
| 4,941,808 A | 7/1990 | Qureshi et al. |
| 5,101,679 A | 4/1992 | Smith et al. |
| 5,163,010 A * | 11/1992 | Klein et al. .................. 700/239 |
| 5,268,166 A | 12/1993 | Barnett et al. |
| 5,277,713 A | 1/1994 | Gelain et al. |
| 5,322,684 A | 6/1994 | Barnett et al. |
| 5,387,200 A | 2/1995 | Kronstadt |
| 5,460,192 A | 10/1995 | McClain |
| 5,494,674 A | 2/1996 | Barnett et al. |
| 5,527,564 A | 6/1996 | Napadow et al. |
| 5,545,140 A | 8/1996 | Conero et al. |
| 5,664,593 A * | 9/1997 | McClain .................. 132/333 |
| 5,704,554 A | 1/1998 | Cooper et al. |
| 5,738,728 A | 4/1998 | Tisone |
| 5,765,761 A | 6/1998 | Law et al. |
| 5,833,751 A | 11/1998 | Tucker |
| 5,863,497 A | 1/1999 | Dirksing |
| 5,922,333 A | 7/1999 | Laughlin |
| 6,003,794 A | 12/1999 | Hartman et al. |
| 6,138,922 A | 10/2000 | Hartman et al. |
| 6,199,557 B1 | 3/2001 | Laughlin |
| 6,227,466 B1 | 5/2001 | Hartman et al. |
| 6,302,122 B1 | 10/2001 | Parker et al. |
| 6,302,662 B1 | 10/2001 | Bensley et al. |
| 6,326,062 B1 | 12/2001 | Noakes et al. |
| 6,387,081 B1 | 5/2002 | Cooper |
| 6,431,189 B1 * | 8/2002 | Deibert ..................... 134/57 R |
| 6,443,164 B1 | 9/2002 | Parker et al. |
| 6,554,208 B1 | 4/2003 | Venuto, Sr. |
| 6,802,830 B1 | 10/2004 | Waters et al. |
| 2003/0127542 A1 | 7/2003 | Cooper |
| 2004/0073186 A1* | 4/2004 | Cameron .................... 604/389 |

FOREIGN PATENT DOCUMENTS

| | | |
|---|---|---|
| EP | 0 031 649 B1 | 9/1984 |
| EP | 0 224 352 B1 | 8/1990 |
| EP | 0 441 501 A1 | 8/1991 |
| EP | 0 468 736 A1 | 1/1992 |
| EP | 0 468 736 B1 | 3/1997 |
| EP | 0 441 501 B1 | 8/1997 |

* cited by examiner

SINGLE-DOSE SPRAY SYSTEM FOR APPLICATION OF LIQUIDS ONTO THE HUMAN BODY

CROSS-REFERENCE TO RELATED APPLICATIONS

This application claims the benefits of and priority to U.S. Provisional Patent Application No. 60/469,289 filed May 9, 2003, the disclosure of which is incorporated by reference.

BACKGROUND OF THE INVENTION

Spray devices for the application of liquids onto human skin and hair are well known. Spray applications are used for many types of medicines, hair treatments, deodorants, lotions, and cosmetic agents. One form of spray device for the application of liquids for skin treatment are hand-held spray devices. Usually these hand-held spray devices are comprised of disposable pressurized can spray applicators having a finger actuated spray valve and nozzle. Non-pressurized hand-held spray applicators are also available consisting of reusable trigger-pump spray devices. These disposable and refillable trigger sprayers are held in one hand at less than a meter away from the skin to treat portions of the body. Container sizes for these types of sprayers are adapted to hold volumes of liquids adequate for multiple applications from a single container. Uniform spray applications of a precise dosage or coverage of an entire body are difficult with these types of hand-held spray applicators.

Other types of hand held applicators are those with liquid containers that use liquid pressure or compressed gas for atomization and propulsion. An example of this type of hand-held applicator is a hand-held air-brush sprayer adapted to be used to dispense cosmetic agents. One disadvantage of such air-brush systems is that the liquid containers are of an inappropriate size, often being too large or too small, to coat an entire person or selected parts of a person. In addition, the refilling process for such devices can be messy.

Another disadvantage of hand-held air-brush systems is that it is difficult for a person to self-apply an even coat to certain body portions, such as the back. To overcome this problem, professional salons and spas offer trained sunless-tanning applicator personnel to apply material carefully over the entire body of the customer. This situation is often inconvenient and uncomfortable for both the personnel and the customer. In addition, since hand-held airbrush applications usually take 10 to 30 minutes, the process can be irritating to the tanning applicator and the customer due to prolonged exposure to the spray environment. Fatigue is also known to occur in the back, arms, and wrists of applicator personnel due to the repetitive motion of the hand-held brushing process.

Applications of cosmetic agents, such as sunless tanning compounds, with hand-held spray devices require very experienced personnel to avoid mistakes which may result in under- or over-application, missed areas, streaks, and runs. Another drawback that limits the practicality and marketplace potential of hand-held cosmetic sprays in which an assistant is needed is the potential inconvenience and embarrassment to the person being coated, since they must stand for the duration of the application in an unclothed or partially unclothed state.

Non-hand-held systems for dispensing liquid to the human body have also been developed. U.S. Pat. No. 1,982,509 describes a prior system for applying treatment media to a living body. U.S. Pat. No. 1,982,509 describes a carrier device which moves up and down and provides for applying a treatment media to a body. However, U.S. Pat. No. 1,982,509 does not describe for the use of removable liquid containers, or for liquid containers adapted to be of a size for applying a single dosage to portions of a human body as provided by embodiments of the present invention.

Automated systems for self-application of a spray mist to the entire body have recently been introduced for sunless tanning. These systems are housed within cabinets or booths to permit enclosure of an adult and provide for hands-free, uniform, self-application in a private setting. U.S. Pat. No. 5,922,333 to Laughlin, U.S. Pat. No. 6,387,081 to Cooper, U.S. Pat. No. 6,302,122 to Parker et al., and U.S. Pat. No. 6,443,164 to Parker et al. each describe automated systems for coating the human body in which a spray chamber is used. In present systems, several spray nozzles are fed from a single large tank containing sunless tanning solution. These automatic spray systems are designed to dispense approximately five to ten tanning sessions per liter of liquid, and generally use a feeder-tank capacity of eight to twenty liters. Since each customer's dose is drawn from a common tank, the customer has no assurance of the amount applied, nor do they have a choice of the type of lotion to be applied for a certain skin type or desired tanning color. It is not currently practical to adapt present automatic systems to dispense a single dosage from an individually sized container because of the wasted volume of spray liquid that resides in the many hoses that are required to feed each of the many spray nozzles. The various embodiments of the present invention provide for a self-application spray device having a liquid container closely connected to a nozzle system and of a size allowing a customer to dispense an appropriate volume of spray solution of their choice.

BRIEF SUMMARY OF THE INVENTION

One embodiment of the present invention is directed to a spray device including at least one nozzle and at least one liquid container where the at least one liquid container is adapted to hold a volume of spray liquid substantially equal to an amount required to apply a single dosage of the spray liquid for coating a surface of a human body. The spray device further includes a liquid channel adapted to connect the at least one liquid container to the at least one nozzle, and a spray valve adapted to cause the spray liquid to flow from the at least one liquid container to the at least one nozzle using the liquid channel. The spray device still further includes a control device adapted to control the operation of the spray device; and mounting means for mounting the spray device to a mounting surface.

Another embodiment of the present invention is directed to a spray device for coating a surface of a human body with a spray liquid. The spray device includes at least one nozzle and at least one liquid container where the at least one liquid container is adapted to hold a volume of spray liquid of less than one liter. The spray device further includes a liquid channel adapted to connect the at least one liquid container to the at least one nozzle and a spray valve adapted to cause the spray liquid to flow from the at least one liquid container to the at least one nozzle using the liquid channel. The spray device still further includes a control device adapted to control the operation of the spray device, and mounting means for mounting the spray device to a mounting surface.

Still another embodiment of the present invention is directed to a spray device including at least one nozzle and at least one removable liquid container where the at least one removable liquid container is adapted to hold a volume of spray liquid substantially equal to an amount required to apply a single dosage of the spray liquid for coating a surface of a human body. The spray device further includes a receiver adapted to receive the at least one removable liquid container, a liquid channel adapted to connect the at least one removable container to the at least one nozzle, and a spray valve adapted to cause the spray liquid to flow from the at least one removable container to the at least one nozzle using the liquid channel. The spray device still further includes a control device adapted to control the operation of the spray device, and mounting means for mounting the spray device to a mounting surface.

Still another embodiment of the present invention is directed to a spray device including at least one nozzle, and at least one liquid container where the at least one liquid container is adapted to hold a volume of spray liquid substantially equal to an amount required to apply a single dosage of the spray liquid for coating a surface of a human body. The spray device further includes a liquid channel adapted to connect the at least one liquid container to the at least one nozzle, and a pressurized gas conduit where the pressurized gas conduit is adapted to connect a source of compressed gas to the at least one nozzle. The spray device further includes a spray valve adapted to cause pressurized gas to flow from the source of pressurized gas to the at least one nozzle using the gas conduit, wherein the flow of pressurized gas to the at least one nozzle facilitates flow of the spray liquid from the at least one liquid container to the at least one nozzle using the liquid channel, a control device adapted to control the operation of the spray device, and mounting means for mounting the spray device to a mounting surface.

DETAILED DESCRIPTION OF THE INVENTION

Figure 1:
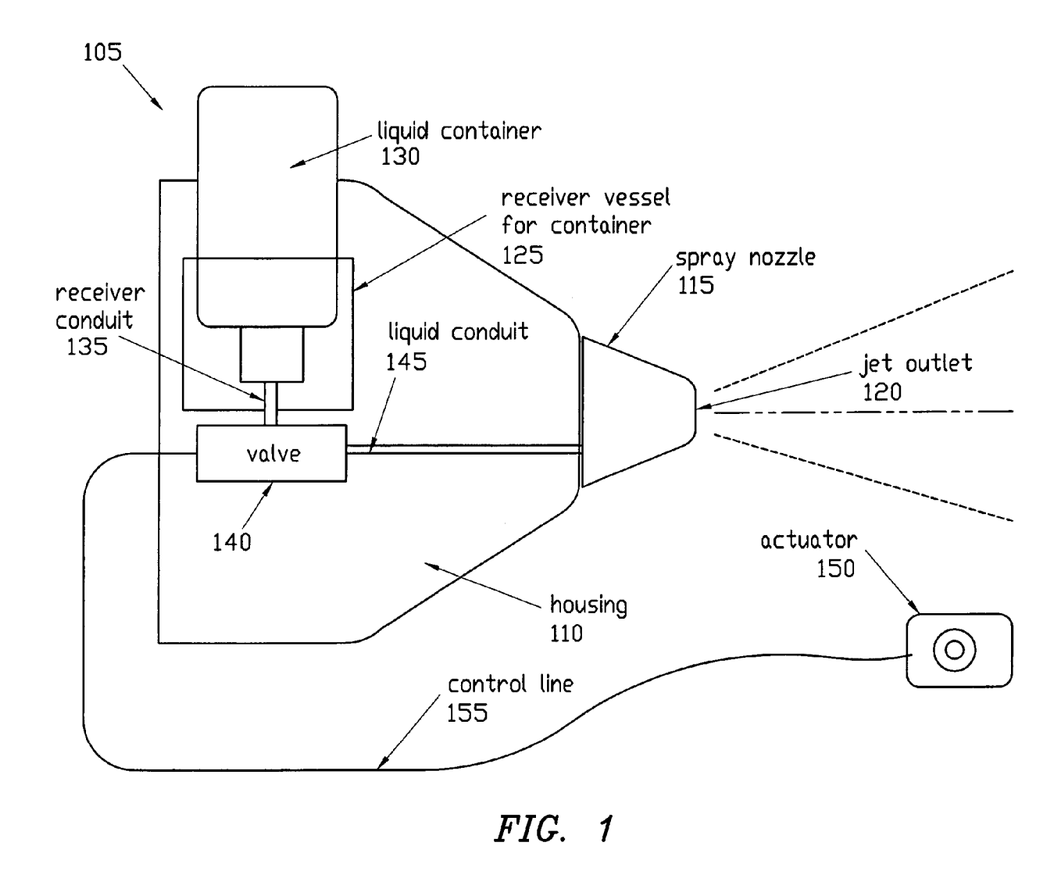
FIG. 1 illustrates a spray device adapted to coat a surface of a human body with a spray liquid in accordance with an embodiment of the present invention.

Referring now to FIG. 1, a spray device adapted to coat a surface of a human body with a spray liquid, such as a sunless tanning compound, in accordance with an embodiment of the present invention is illustrated. The spray device 105 includes a housing 110 having an attached spray nozzle 115. The spray nozzle 115 includes a jet outlet 120 for dispensing a spray of liquid to cover a portion of a human body. In another embodiment of the present invention, the spray nozzle 115 may be comprised of an electrostatic spray nozzle adapted to produce electrostatically charged droplets of the spray liquid. Many types of electrostatic spray nozzles exist in the prior art, of which many are suitable for use in embodiments of the present invention.

The housing 110 contains a receiver vessel 125 adapted to receive and support an inserted removable liquid container 130. In accordance with an embodiment of the present invention, the removable liquid container 130 is adapted to be disposable after use. In accordance with one embodiment of the present invention, the receiver vessel 125 may be of a shape so that it mates with the outside shape of the removable liquid container 130 to properly orient the removable liquid container 130 within the receiver vessel 125, as well as ensure that the correct container is used in the spray device 105. Upon insertion of the removable liquid container 130 into the receiver vessel 125, a receiver conduit 135 connected to a liquid valve 140 punctures a liquid seal in the removable liquid container 130. In accordance with an embodiment of the present invention, the removable liquid container 130 is adapted to be of a size to contain an amount of liquid substantially equal to that required to apply a single dosage of the liquid to be sprayed to coat a surface of a human body. For example, this volume may be in the range of 100 ml to 150 ml. The amount of liquid substantially equal to that required to apply a single dosage may vary in accordance with the type of liquid and efficiency of the spray device, for example, between a range of 100 ml to 500 ml. In accordance with still another embodiment of the present invention, the removable liquid container 130 may comprise a disposable liquid container or a refillable liquid container.

Upon opening of the liquid valve 140, the liquid in the removable liquid container 130 is allowed to flow through a liquid conduit 145, or a liquid channel, to the spray nozzle 115, and exit the spray nozzle through jet outlet 120 in the form of a liquid spray. The removable liquid container 130 may optionally be pressurized or vented to facilitate the dispensing of liquid from the liquid container 130. In addition, the receiver vessel 125 may optionally be provided with a vent. In an embodiment of the present invention, the liquid conduit 145 is adapted to be of a length such that the distance that the liquid is required to flow between the liquid valve 140 and the spray nozzle 115 is short. In accordance with an embodiment of the present invention, the length of the liquid conduit 145 is less than approximately 160 millimeters. In accordance with another embodiment of the present invention, the liquid conduit 145 is adapted to hold less than 20 ml of liquid. At least one advantage provided by the liquid conduit 145 being of a relatively short length is that during a single tanning session, sequential use of multiple removable liquid containers can be used without requiring the purging of the liquid conduit 145. For example, a particular customer may desire to have a pre-tanning compound from a first removable liquid container be applied, and then subsequently have a tanning compound from a second removable liquid container be applied. In accordance with other embodiments of the present invention, the liquid conduit 145 may be adapted to be contained within the liquid valve 140, the spray nozzle 115, or a fitting.

In accordance with an embodiment of the present embodiment, the spray device 105 further includes an actuator 150 connected to the liquid valve 140 via a control line 155 which functions as a control device to allow an operator to control operation of the liquid valve 140. In accordance with various embodiments, the actuator 150 may be comprised of an electrical switch, a hand-held actuator or remote control, mounted on the housing 110 of the spray device 105, or mounted on a wall or a floor near the person to be coated by the liquid spray, thereby providing remote activation of the spray device 105 by hand or foot while allowing a person to be coated to stand at an optimum distance away from the spray nozzle 115. The remote activation provided by the actuator 150 allows, for example, for a person being coated to move body parts or completely turn in order to achieve uniform coverage. It should be understood that activation of the spray device 105 may be controlled either by an operator or the person to be coated.

In accordance with still other embodiments of the present invention, it may not be necessary to include a control line 155 to connect the actuator 150 to the valve 140. Alternately, the actuator 150 can be adapted to control the valve 140 via a wireless connection, such as an infrared or other light signal, a radio signal, a motion signal, or a voice activation or another sound signal. The actuator 150 can optionally be provided with an electrical connection to connect an operator to earth ground. In still other embodiments, the actuator 150 may comprise a hydraulic flow device or a pneumatic flow device connected to the spray device 105 via a tube.

In accordance with an embodiment of the present invention, after activation of the spray device 105 via actuator 150, the spray device 105 continues to spray the spray liquid until a single dosage of the spray liquid is dispensed and the removable liquid container 130 is substantially empty of the spray liquid. In accordance with another embodiment of the present invention, the spray of the spray liquid from the spray device 105 may be momentarily paused during the spray operation in order that the subject being sprayed can reposition themselves, or be automatically repositioned, with respect to the spray device 105. For example, during a single spraying operation, the spray of spray liquid from the spray device 105 may be paused one or more times, the subject may be instructed to turn his or her body in a new orientation, and then the spray of spray liquid from the spray device 105 may be resumed. Upon final completion of the spraying operation, the liquid container is substantially empty of the spray liquid. In accordance with still other embodiments of the present invention, deactivation of the spray device 105 may be performed either through the use of the actuator 150 or automatically after a predetermined time has elapsed, or based on a detected emptying of the liquid container.

In accordance with another embodiment of the present invention, the removable liquid container 130 may be adapted to hold a volume of spray liquid equal to that required to hold multiples of a single dosage of the spray liquid while still having a size small enough such that it may be easily installed and removed, as well as emptied before spoilage may occur. For example, in an application in which a typical single dosage of spray liquid is equal to approximately 100 ml to 150 ml, the removable liquid container 130 may be adapted to hold a volume of spray liquid of less than or equal to approximately one liter. At least one advantage provided by this embodiment is that multiple dosages can be dispensed from a single removable liquid container while still allowing the removable liquid container contents to be depleted before spoilage occurs.

Figure 2:
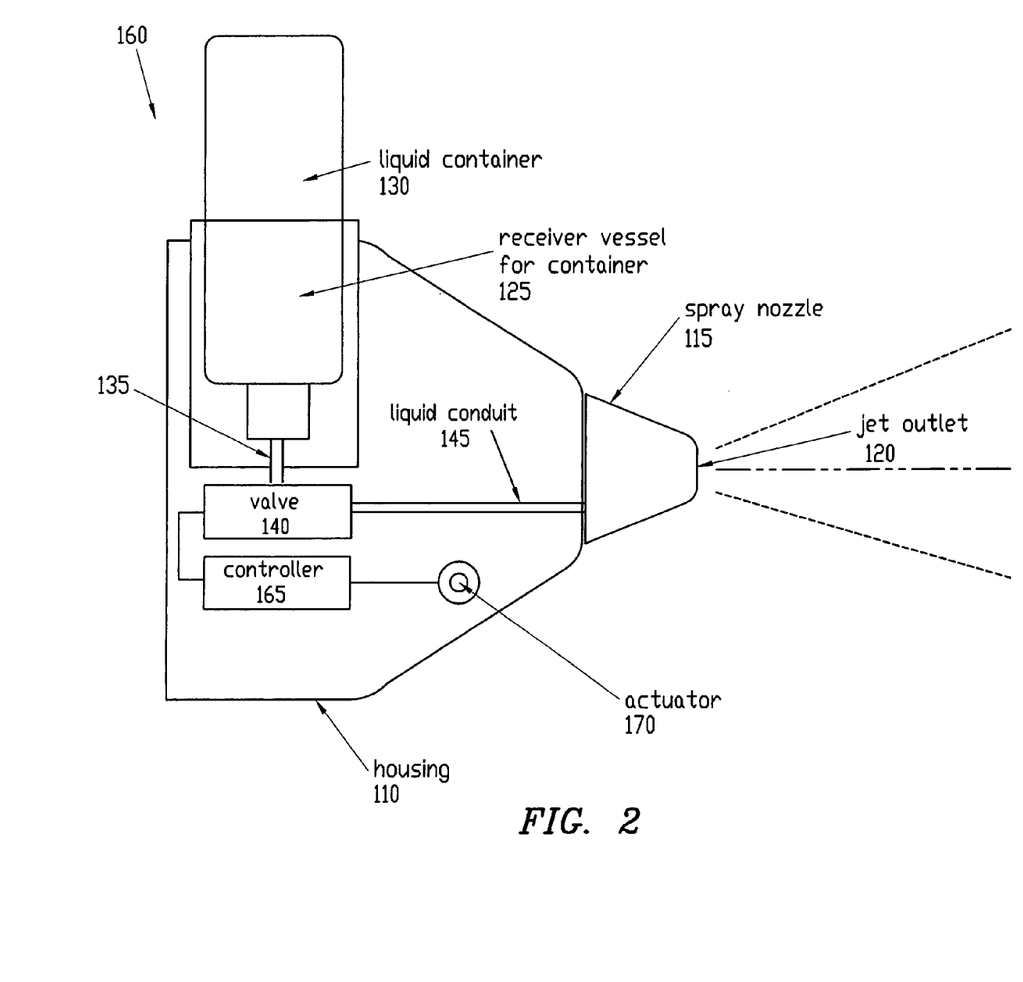
FIG. 2 illustrates a spray device adapted to coat a surface of a human body with a spray liquid in accordance with another embodiment of the present invention.

Referring now to FIG. 2, a spray device adapted to coat a surface of a human body with a spray liquid, such as a sunless tanning compound, in accordance with another embodiment of the present invention is illustrated. The spray device 160 includes a housing 110, a spray nozzle 115, a jet outlet 120, a receiver vessel 125, a removable liquid container 130, a receiver conduit 135, a liquid valve 140, and a liquid conduit 145 similar to or the same as those described in relation to FIG. 1. No further description of these components is provided except when necessary.

In accordance with the embodiment of FIG. 2, the spray device 160 further includes a controller 165 connected to the liquid valve 140. The controller 165 functions to control the opening and closing of the liquid valve 140. In accordance with one embodiment of the present invention, the controller 165 may comprise an electrical or pneumatic circuit incorporating a timer to control spray duration. In accordance with another embodiment of the present invention, the controller may comprise a programmable controller device to activate a variable spray duration. In accordance with the present embodiment the spray device 160 may further include an actuator 170 to initiate operation of the controller 165. Although in the embodiment of FIG. 2 the controller 165 and actuator 170 are shown mounted to a surface of the housing 110, it should be understood that the controller 165 and actuator 170 may be incorporated within a remote control device adapted to be held in the hand.

In accordance with an embodiment of the present invention, the controller 165 may be used to start the spray device 160 immediately, or alternately cause a delay prior to the start of spraying. In an example operation of the present embodiment, a button of actuator 170 may be pressed to initiate the controller 165. The controller 165 then delays for a predetermined delay period, such as a few seconds, to allow the person being sprayed to move into the proper position in relation to the jet outlet 120. After the delay period, the controller 165 activates the liquid valve 140 and the spray device 160 begins to spray until a single dosage is dispensed and the removable liquid container 130 is substantially empty of the spray liquid. In other embodiments of the present invention other means of initiating a control sequence may be used, such as sensing the insertion of the liquid container into the spray device.

Figure 3:
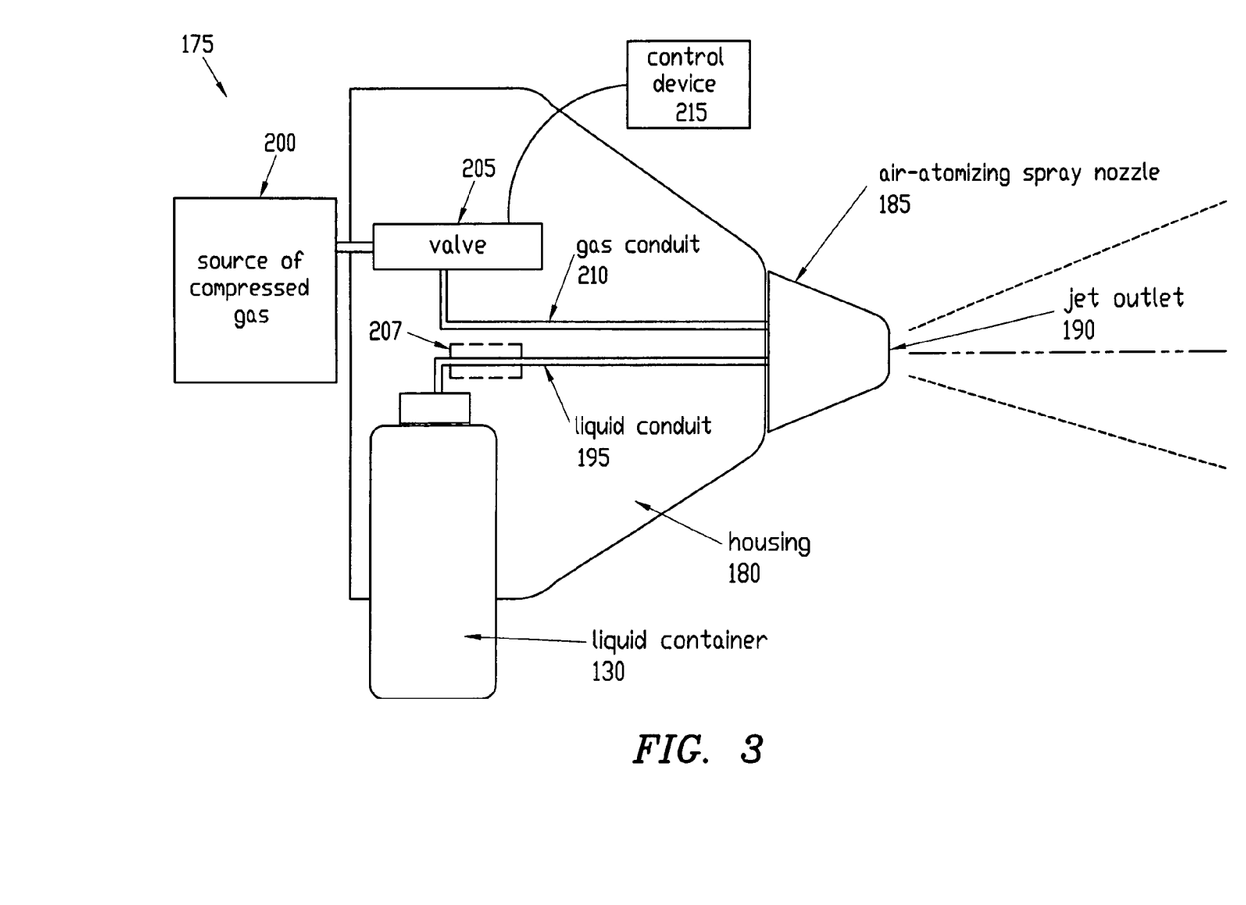
FIG. 3 illustrates an air-atomizing spray device adapted to coat a surface of a human body with a spray liquid in accordance with another embodiment of the present invention.

Referring now to FIG. 3, an air-atomizing spray device adapted to coat a surface of a human body with a spray liquid, such as a sunless tanning compound, in accordance with another embodiment of the present invention is illustrated. The spray device 175 includes a housing 180 having an attached air-atomizing spray nozzle 185. The air-atomizing spray nozzle 185 includes a jet outlet 190 for dispensing a spray of liquid to cover a portion of a human body. It should be understood that while the present embodiment is described as having a single air-atomizing spray nozzle 185, multiple spray nozzles may be used. In another embodiment of the present invention, the air-atomizing spray nozzle 185 may be comprised of an electrostatic spray nozzle adapted to produce electrostatically charged droplets of the spray liquid. Many types of electrostatic spray nozzles exist in the prior art, of which many are suitable for use in embodiments of the present invention.

The housing 180 is adapted to receive and support an inserted removable liquid container 130. In accordance with an embodiment of the present invention, the removable liquid container 130 is adapted to be of a size to contain an amount of liquid substantially equal to that required to apply a single dosage of the liquid to be sprayed to coat a surface of a human body. For example, this volume may be in the range of 100 ml to 150 ml. The amount of liquid substantially equal to that required to apply a single dosage may vary in accordance with the type of liquid and efficiency of the spray device, for example, between a range of 100 ml to 500 ml. In accordance with still another embodiment of the present invention, the removable liquid container 130 may comprise a disposable liquid container or a refillable liquid container.

Upon insertion of the removable liquid container 130 into the housing 180, a liquid conduit 195 connects the removable liquid container 130 to the air-atomizing spray nozzle 185. The spray device 175 is further adapted to support the connection of a source of compressed gas 200 to a gas valve 205. The gas valve 205 is further connected to the air-atomizing spray nozzle 185 via a gas conduit 210. A control device 215 is connected to the gas valve 205 to control operation of the gas valve 205.

Upon opening of the gas valve 205, gas from the source of compressed gas 200 is allowed to flow to air-atomizing nozzle 185. Through a Venturi action of the gas flowing to the air-atomizing nozzle 185, liquid in the removable liquid container 130 is pulled through the liquid conduit 195 to the spray nozzle 185, and exits the spray nozzle 185 through jet outlet 190 in the form of an air-atomized liquid spray. The removable liquid container 130 may optionally be pressurized or vented to facilitate the dispensing of liquid from the liquid container 130. In an embodiment of the present invention, the liquid conduit 195 is adapted to be of a length such that the distance that the liquid is required to flow between the removable liquid container 130 and the spray nozzle 185 is short. In accordance with an embodiment of the present invention, the length of the liquid conduit 195 is less than approximately 160 millimeters. In accordance with another embodiment of the present invention, the liquid conduit 195 is adapted to hold less than 20 ml of liquid. In an alternate embodiment of the present invention, a liquid valve 207 may additionally be used to control flow of liquid in the liquid conduit 195, although it is not required. In accordance with other embodiments of the present invention, the liquid conduit 195 may be adapted to be contained within the liquid valve 207, the spray nozzle 185, or a fitting.

In accordance with an embodiment of the present embodiment, the control device 215 may comprise a remote control, an actuator, a timer, or a programmable controller. In accordance with various embodiments, the control device 215 may be adapted to be a hand-held actuator or remote control, mounted on the housing 180 of the spray device 175, or mounted on a wall or a floor near the person to be coated by the liquid spray, thereby providing remote activation of the spray device 175 by hand or foot while allowing a person to be coated to stand at an optimum distance away from the air-atomizing spray nozzle 185. The remote activation provided by the control device 215 allows, for example, for the person being coated to move body parts or completely turn in order to achieve uniform coverage. It should be understood that activation of the spray device 175 may be controlled either by an operator or the person to be coated. In accordance with still other embodiments of the present invention, the control device 215 may be adapted to control the gas valve 205 via a wireless connection, such as an infrared or other light signal, a radio signal, a motion signal, or a voice activation or another sound signal. In still other embodiments, the control device 215 may comprise a hydraulic flow device or a pneumatic flow device connected to the spray device 175 via a tube. In still another embodiment of the present invention, the gas valve 205 may be comprised of a mechanical toggle valve with the toggle valve and associated conduits positioned outside of the housing 180 and held as a hand-held remote control, or positioned in a location convenient to the operator, such as mounted on a wall or floor.

Figure 4:
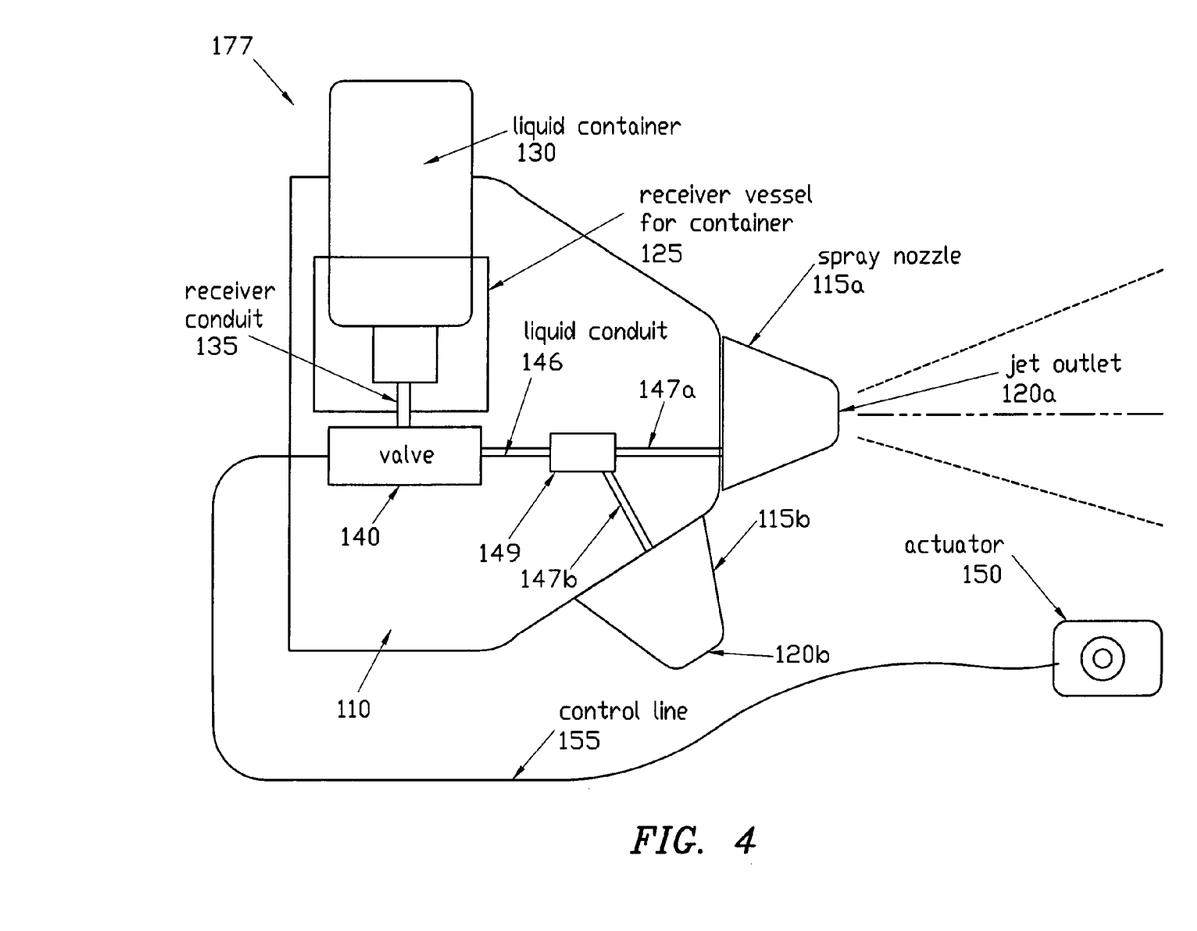
FIG. 4 illustrates a multi-nozzle spray device adapted to coat a surface of a human body with a spray liquid in accordance with another embodiment of the present invention.

In accordance with an embodiment of the present invention, after activation of the spray device 175 via control device 215, the spray device 175 continues to spray the spray liquid until a single dosage of the spray liquid is dispensed and the removable liquid container 130 is substantially empty of the spray liquid. In accordance with another embodiment of the present invention, the spray of the spray liquid from the spray device 175 may be momentarily paused during the spray operation in order that the subject being sprayed can reposition themselves, or be automatically repositioned, with respect to the spray device 175. For example, during a single spraying operation, the spray of spray liquid from the spray device 175 may be paused one or more times, the subject may be instructed to turn his or her body in a new orientation, and then the spray of spray liquid from the spray device 175 may be resumed. Upon final completion of the spraying operation, the liquid container is substantially empty of the spray liquid. In accordance with still other embodiments of the present invention, deactivation of the spray device 175 may be performed either through the use of the control device 215 or automatically after a predetermined time has elapsed.

Referring now to FIG. 4, a multi-nozzle spray device adapted to coat a surface of a human body with a spray liquid, such as a sunless tanning compound, in accordance with another embodiment of the present invention is illustrated. The spray device 177 includes a housing 110, a receiver vessel 125, a removable liquid container 130, a receiver conduit 135, a liquid valve 140, an actuator 150, and a control line 155 similar to or the same as those described in relation to FIG. 1. No further description of these components is provided except when necessary.

The spray device 177 further includes a liquid conduit 146 connecting the liquid valve 140 to a metering device 149. The spray device 177 further includes a first nozzle conduit 147*a* connecting the metering device 149 to a first spray nozzle 115*a* having a first jet outlet 120*a*, and a second nozzle conduit 147*b* connecting the metering device 149 to a second spray nozzle 115*b* having a second jet outlet 120*b*. The metering device 149 is adapted to control the flow of fluid through the first nozzle conduit 147*a* and the second nozzle conduit 147*b*. In accordance with an embodiment of the present invention, the metering device 149 is adapted to control the flow of fluid such that equal volumes of spray liquid are provided to each of the first spray nozzle 115*a* and the second spray nozzle 115*b* during the spraying operation. In accordance with another embodiment of the present invention, the metering device 149 may be adapted to provide a different measured volume of liquid to each of the first spray nozzle 115*a* and the second spray nozzle 115*b*. In accordance with an embodiment of the present invention, the metering device 149 can be comprised of a solenoid, pump, or any other suitable liquid metering device. In accordance with still another embodiment of the present invention, separate metering devices may be provided in each of the spray nozzles. Although the present embodiment is illustrated using two spray nozzles, it should be understood that any number of a plurality of liquid nozzles may be used.

In an embodiment of the present invention, the liquid conduit 146, the first nozzle conduit 147*a*, and the second nozzle conduit 147*b* are all adapted to be of a length such that the distance that the liquid is required to flow between the liquid valve 140 and the first spray nozzle 115*a* and the second spray nozzle 115b is short enough that purging of the spray device 177 is not necessary between applications.

Figure 5:
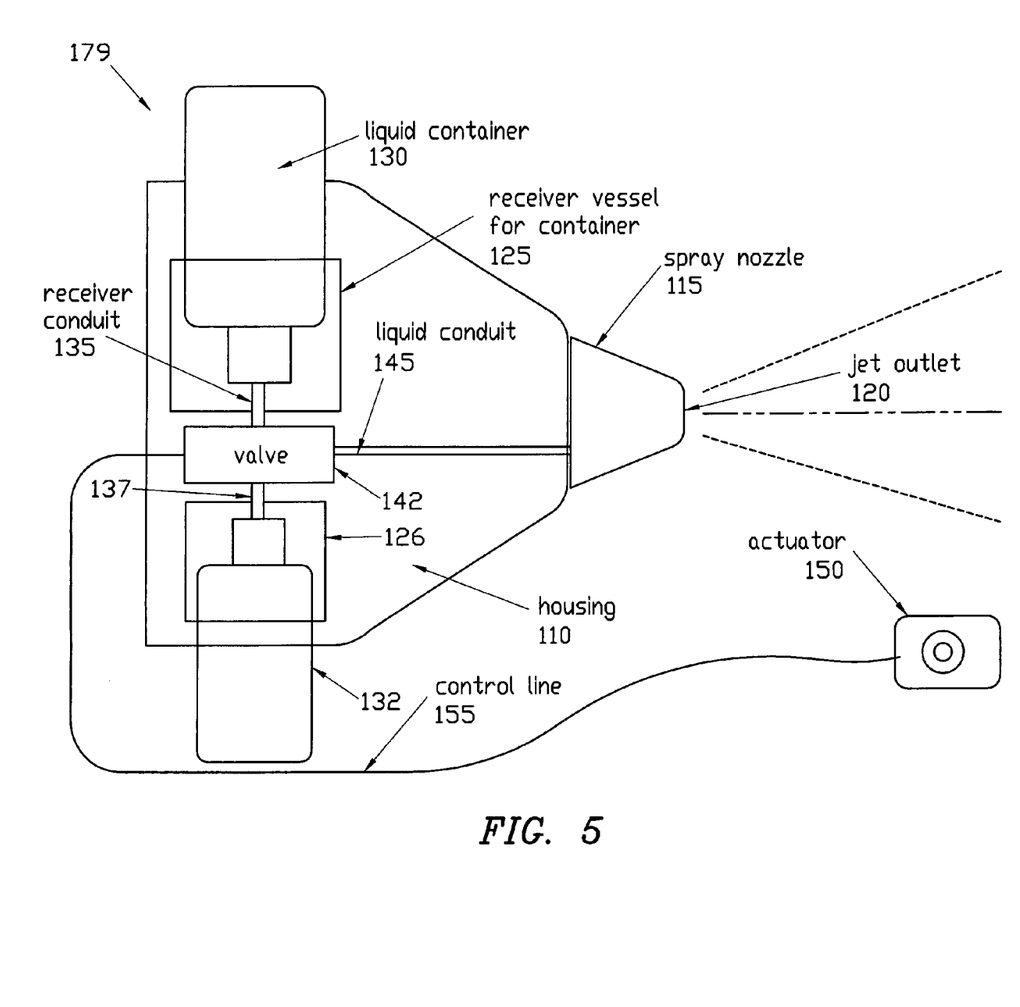
FIG. 5 illustrates a multi-receiver vessel spray device adapted to coat a surface of a human body with a spray liquid in accordance with another embodiment of the present invention.

Referring now to FIG. 5, a multi-receiver vessel spray device adapted to coat a surface of a human body with a spray liquid, such as a sunless tanning compound, in accordance with another embodiment of the present invention is illustrated. In accordance with the present embodiment, the spray device 179 includes a housing 110, a spray nozzle 115, a jet outlet 120, a receiver vessel 125, a removable liquid container 130, a receiver conduit 137, and a liquid conduit 145 similar to or the same as those described in relation to FIG. 1. No further description of these components is provided except when necessary. The receiver conduit 135 is further connected to a liquid valve 142.

The spray device 179 further includes another receiver vessel 126 adapted to receive and support another removable liquid container 132. In accordance with an embodiment of the present invention, the removable liquid container 132 is adapted to be refillable or disposable after use. In accordance with one embodiment of the present invention, the receiver vessel 126 may be of a shape so that it mates with the outside shape of the removable liquid container 132 to properly orient the removable liquid container 132 within the receiver vessel 126, as well as ensure that the correct container is used in the spray device 179. Upon insertion of the removable liquid container 132 into the receiver vessel 126, a receiver conduit 137 connected to the liquid valve 142 punctures a liquid seal in the removable liquid container 132. In accordance with an embodiment of the present invention, the removable liquid container 132 is adapted to be of a size to contain an amount of liquid substantially equal to that required to apply a single dosage of the liquid to be sprayed to coat a surface of a human body.

In accordance with the embodiment of FIG. 5, the liquid valve 142 is adapted to selectively allow the flow of spray liquid from one of the removable liquid container 130 and the removable liquid container 132 through the liquid conduit 145 to the spray nozzle 115, and exit the spray nozzle 115 through jet outlet 120 in the form of a liquid spray. In accordance with one embodiment of the present invention, the selection of which one of the spray liquids from removable liquid container 130 and the removable liquid container 132 that is allowed by the liquid valve 142 to flow to the spray nozzle 115 may be performed by an operator using the actuator 150.

The embodiment of FIG. 5 provides for the use of multiple removable liquid containers in a single tanning session. In accordance with one embodiment, the contents of each of the removable liquid containers may be applied sequentially. For example, a particular customer may desire to have a pre-tanning compound from a first removable liquid container be applied, and then subsequently have a tanning compound from a second removable liquid container be applied. Switching between the first removable liquid container and the second removable liquid container may be performed through the use of the actuator 150 or automatically after a predetermined time has elapsed, or based on a detected emptying of the removable liquid container. In accordance with still another embodiment of the present invention, the liquid valve 142 may adapted to allow the flow of spray liquid from the first removable liquid container and the second removable liquid container simultaneously, thus allowing for mixing of the solutions during application. Although the present embodiment is illustrated using two removable liquid containers, it should be understood that any number of a plurality of removable liquid containers may be used.

Figure 6:
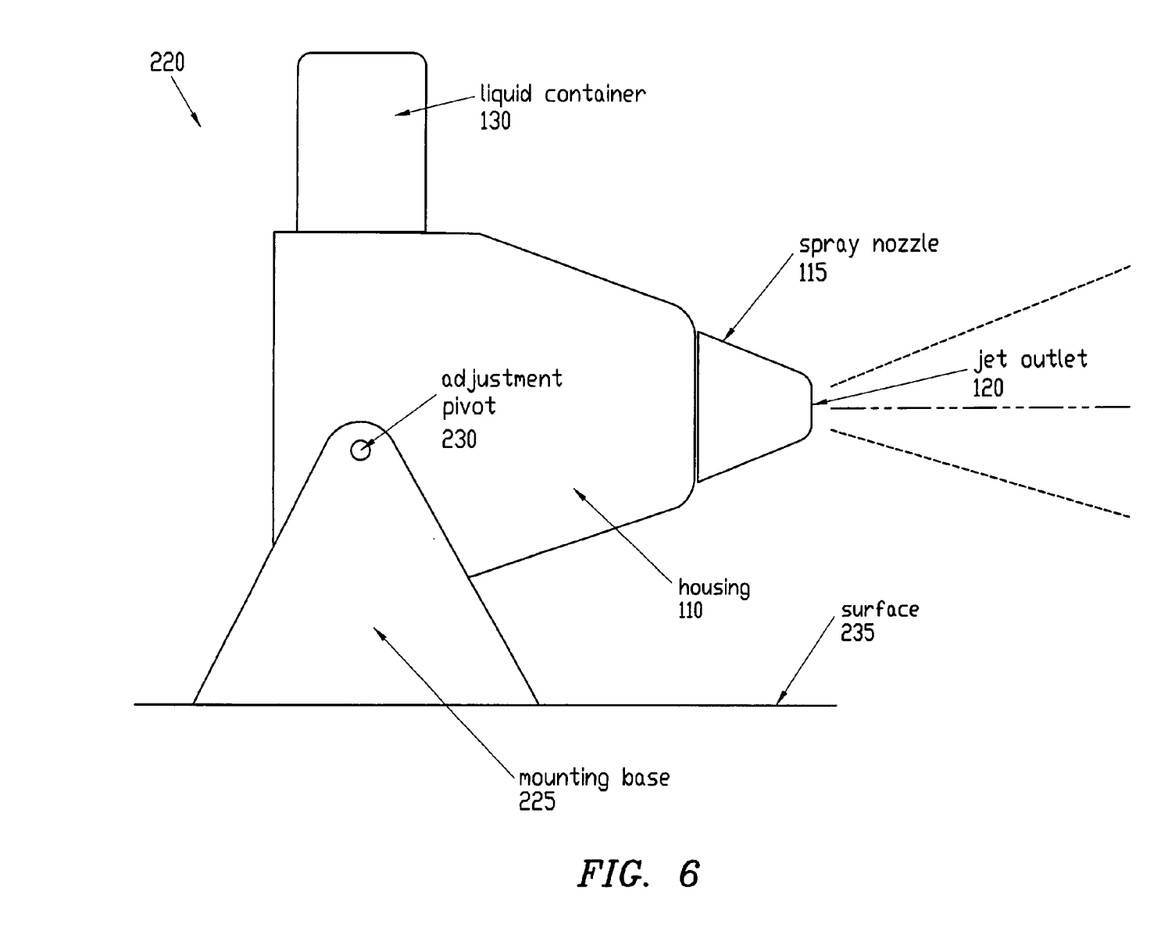
FIG. 6 illustrates an embodiment of a mounting arrangement for use with at least one embodiment of a spray device of the present invention.

Referring now to FIG. 6, an embodiment of a mounting arrangement for use with at least one embodiment of a spray device of the present invention is illustrated. The spray device 220, which may be comprised of any of the embodiments of the spray devices as described in reference to FIGS. 1-5, is adapted to be mounted to a mounting base 225 via an adjustment pivot 230. The mounting base 225 is adapted to be mounted on a horizontal mounting surface 235, such as a table top, counter, or stand. The adjustment pivot 230 is adapted to act as a swivel point to allow angular adjustment of the spray device 220 to a desired spray angle. Accordingly, the adjustment pivot 230 allows a user or operator of the spray device 220 to position the spray device 220 in order to set the spray angle of the spray device 220 to more accurately direct the liquid spray towards a desired area of the human body. It should be understood that other means for mounting the various embodiment of the spray device of the present invention may be used, such as using non-adjustable mounting means or a gantry system.

Figure 7:
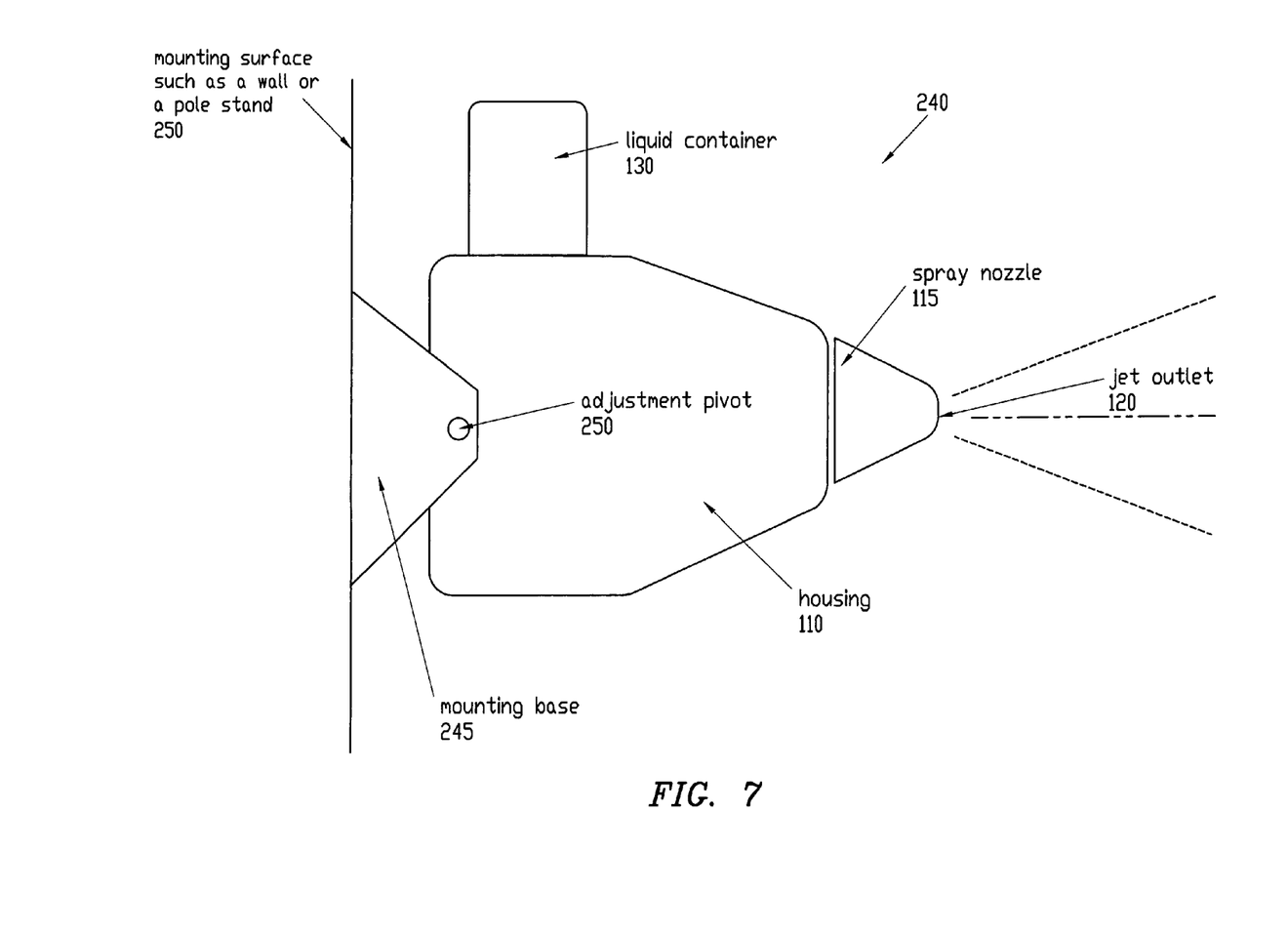
FIG. 7 illustrates another embodiment of a mounting arrangement for use with at least one embodiment of a spray device of the present invention.

Referring now to FIG. 7, another embodiment of a mounting arrangement for use with at least one embodiment of a spray device of the present invention is illustrated. The spray device 240, which may be comprised of any of embodiments of the spray devices as described in FIGS. 1-5, is adapted to be mounted to a mounting base 245 via an adjustment pivot 250. The mounting base 245 is adapted to be mounted on a vertical mounting surface 250, such as a wall or a pole stand. The adjustment pivot 250 is adapted to act as a swivel point to allow angular adjustment of the spray device 240 to a desired spray angle. Accordingly, the adjustment pivot 250 allows a user or operator of the spray device 240 to position the spray device 240 in order to set the spray angle of the spray device 240 to more accurately direct the liquid spray towards a desired area of the human body. It should be understood that other means for mounting the various embodiment of the spray device of the present invention may be used, such as using non-adjustable mounting means or a gantry system.

Several advantages are provided by various embodiment of the spray device of the present invention. For example, in a self-tanning application, the use of small, individual liquid containers rather than bulk tanks allows for a customer to choose from among a variety of self-tanning solutions. In addition, it allows for the customer to choose from a variety of pre-treatment and post-treatment lotions that improve the tanning process, such as lotions, dehydrants, accelerators, and fragrances to mask the DHA chemical odor present in certain self-tanning solutions. The use of small individual liquid containers of various volumes, allows the liquid volume of a single application to be readily adjusted to match a particular individual body size.

Another advantage provided by embodiments of the present invention is that the risk of a poor tanning result is reduced since the usage of a single application liquid container prevents the rapid spoilage which occurs in larger tanks of sunless tanning compounds after they are opened. An additional advantage that may be provided is that the customer may be ensured of a fresh solution of sunless tanning compound for each tanning experience. A further advantage is that may be provided is that the customer and salon personnel are reassured that the correct dosage is being applied by the spray device during each tanning session. A further advantage that may be provided by embodiments of the present invention is that the need for maintenance is reduced, and safety and convenience can be improved for salon personnel since large tanks do not have to be moved or poured. Another advantage provided by various embodiment of the present invention is that overall system reliability is improved by eliminating the use of long hoses from tanks to nozzles. In addition, the close proximity of the removable liquid container to the nozzle allows the use of shorter hoses which reduces or eliminates the need for purging the hoses when changing containers, thus enabling the spray device to be self-cleaning. Still another advantage that may be provided by embodiments of the present invention is that it allows application to selected body parts, for example, application to the face or legs.

Although a preferred embodiment of the method and apparatus of the present invention has been illustrated in the accompanying Drawings and described in the foregoing Detailed Description, it is understood that the invention is not limited to the embodiment disclosed, but is capable of numerous rearrangements, modifications, and substitutions without departing from the spirit of the invention as set forth and defined by the claims.

What is claimed is:

1. A spray device comprising:
   at least one nozzle;
   a housing supporting the at least one nozzle;
   a receiver vessel within the housing, the receiver vessel configured to receive a user inserted liquid container, the received liquid container sized to contain, when filled, a maximum volume of spray liquid not to exceed that which is substantially equal to an amount required to apply a single dosage of the spray liquid for coating a surface of a human body;
   a liquid channel adapted to connect the received liquid container to the at least one nozzle;
   a spray valve controlling spraying of the spray liquid received from the received liquid container by the at least one nozzle; and
   a control device which controls the operation of the spray device to perform a single spraying operation with respect to coating the surface of the human body, at the completion of which the liquid container is substantially empty of the spray liquid.

2. The spray device of claim 1, wherein the liquid container comprises a removable liquid container.

3. The spray device of claim 1, wherein the liquid container comprises a disposable liquid container.

4. The spray device of claim 1, wherein the liquid container comprises a refillable liquid container.

5. The spray device of claim 1, wherein the spray liquid comprises a sunless tanning compound.

6. The spray device of claim 1, further including means for mounting the housing to a mounting surface wherein the mounting means includes means for making an angular adjustment of the housing.

7. The spray device of claim 1, wherein the control device comprises a remote control.

8. The spray device of claim 7, wherein the remote control is connected to the spray device by a wire.

9. The spray device of claim 7, wherein the remote control is connected to the spray device via a tube.

10. The spray device of claim 7, wherein the remote control is voice activated.

11. The spray device of claim 7, wherein the remote control operates to control the operation of the spray valve via at least one of a light signal, a radio signal, a motion signal, and a sound signal.

12. The spray device of claim 7, wherein the remote control device comprises at least one of a hydraulic flow device and a pneumatic flow device.

13. The spray device of claim 1, wherein the control device comprises an automatic control device.

14. The spray device of claim 13, wherein the automatic control device comprises at least one of a timer and a programmable controller.

15. The spray device of claim 13, wherein operation of the automatic control device is initiated by an electrical switch.

16. The spray device of claim 1, wherein the control device is further adapted to electrically connect an operator of the control device to a ground.

17. The spray device of claim 1, wherein the at least one nozzle comprises a plurality of nozzles, and the spray device further comprises a metering device adapted to contiol the flow of spray liquid through the plurality of nozzles.

18. The spray device of claim 1 further comprising:

a pressurized gas conduit, the pressurized gas conduit adapted to connect a source of compressed gas to the at least one nozzle through the valve, wherein the flow of pressurized gas to the at least one nozzle facilitates flow of the spray liquid from the liquid container to the at least one nozzle using the liquid channel.

19. The spray device of claim 1, wherein the maximum volume of spray liquid is in a range of 100 milliliters to 500 milliliters.

20. The spray device of claim 1, wherein the maximum volume of spray liquid is in a range of 100 milliliters to 150 milliliters.

21. A spray device comprising:

at least one nozzle;

a housing supporting the at least one nozzle;

a receiver vessel within the housing to receive a removable liquid container having an open end closed by a liquid seal, the received liquid container sized to contain, when filled, a maximum volume of spray liquid not to exceed that which is substantially equal to an amount required to apply a single dosage of the spray liquid for coating a surface of a human body during a single spraying operation, at the completion of which the liquid container is substantially empty of the spray liquid;

a receiver conduit placed within the receiver vessel and adapted to puncture the liquid seal of the received at least one removable liquid container;

a liquid channel connecting the received liquid container to the at least one nozzle; and a spray valve, wherein activation of the spray valve causes spraying of the spray liquid received from the received liquid container by the at least one nozzle.

22. The spray device of claim 21, wherein an inside shape of the receiver vessel is similar to an outside shape of the removable liquid container.

23. The spray device of claim 21, wherein the receiver vessel includes an air vent.

24. The spray device of claim 21, wherein the removable liquid container includes an air vent.

25. The spray device of claim 21, wherein the removable liquid container comprises a disposable liquid container.

26. The spray device of claim 21, wherein the removable liquid container comprises a refillable liquid container.

27. The spray device of claim 21, wherein the spray liquid comprises a sunless tanning compound.

28. The spray device of claim 21, further comprising means for mounting the housing to a mounting surface wherein the mounting means comprises means for making an angular adjustment of the housing.

29. The spray device of claim 21, further comprising a control device adapted to control the operation of the spray device.

30. The spray device of claim 29, wherein the control device comprises a remote control.

31. The spray device of claim 29, wherein the control device comprises an automatic control device.

32. The spray device of claim 21, wherein the maximum volume of spray liquid is in a range of 100 milliliters to 500 milliliters.

33. The spray device of claim 21, wherein the maximum volume of spray liquid is in a range of 100 milliliters to 150 milliliters.

34. A system for coating a surface of a human body with a spray liquid comprising:
   a liquid container sized to contain, when filled, a maximum volume of spray liquid not to exceed that which is substantially equal to an amount required to spray apply a single dosage of the spray liquid for coating a surface of a human body;
   a spray system which receives the liquid container, comprising:
      at least one nozzle;
      a housing to which the nozzle is mounted and including an opening in the housing;
      a receiver vessel within the housing for receiving an end of the liquid container which is inserted by a user through the opening in the housing;
      a liquid channel connecting the received liquid container to the at least one nozzle;
      a spray valve controlling spraying of the spray liquid from the received liquid container by the at least one nozzle; and
      a controller that controls spray system operation to perform a single user spraying operation with respect to coating the surface of the human body of the user, at the completion of which the received liquid container is substantially empty of the spray liquid.

35. The system of claim 34, wherein the liquid container comprises a removable liquid container.

36. The system of claim 34, wherein the liquid container comprises a disposable liquid container.

37. The system of claim 34, wherein the liquid container comprises a refillable liquid container.

38. The system of claim 34, wherein the spray liquid comprises a sunless tanning compound.

39. The system of claim 34, wherein the maximum volume of spray liquid in the range of 100 milliliters to 500 milliliters.

40. The system of claim 34, wherein the maximum volume of spray liquid in the range of 100 to 150 milliliters.

41. A spray device for coating a surface of a human body with a spray liquid comprising:
   at least one nozzle;
   a housing to which the nozzle is mounted and including an opening in the housing;
   a receiver vessel within the housing for receiving an end of a liquid container which is inserted by a user through the opening in the housing;
   a liquid channel connecting the received liquid container to the at least one nozzle;
   a spray valve controlling spraying of the spray liquid from the received liquid container by the at least one nozzle; and
   a controller that controls spray device operation to perform a single user spraying operation with respect to coating the surface of the human body of the user, at the completion of which the received liquid container is substantially empty of the spray liquid.

42. The device of claim 41 wherein the controller stops the single spraying operation upon detecting an emptying of the inserted liquid container.

43. The device of claim 41 wherein the controller stops the single spraying operation upon detecting an elapsing of a predetermined time period.

44. The device of claim 41, wherein an inside shape of the receiver vessel is similar to an outside shape of the liquid container.

45. The device of claim 41, wherein the liquid container comprises a disposable liquid container.

46. The device of claim 41, wherein the liquid container comprises a refillable liquid container.

47. The device of claim 41, wherein the spray liquid comprises a sunless tanning compound.

48. The device of claim 41 wherein the spray valve is located on an air line supplying air to the nozzle.

49. The device of claim 41 wherein the spray valve is located on the liquid channel.

* * * * *

UNITED STATES PATENT AND TRADEMARK OFFICE
CERTIFICATE OF CORRECTION

| | | |
|---|---|---|
| PATENT NO. | : 7,387,684 B2 | |
| APPLICATION NO. | : 10/841396 | |
| DATED | : June 17, 2008 | |
| INVENTOR(S) | : Steven C. Cooper et al. | |

It is certified that error appears in the above-identified patent and that said Letters Patent is hereby corrected as shown below:

Column 12, claim 17, line 13, replace the word [contiol] with the word -- control --.

Signed and Sealed this
Second Day of August, 2011

David J. Kappos
*Director of the United States Patent and Trademark Office*